United States Patent [19]

Creeger

[11] 4,261,835
[45] Apr. 14, 1981

[54] THIN LAYER AND PAPER CHROMATOGRAPHY CONES

[76] Inventor: Samuel M. Creeger, 7503 Dartmouth Ave., College Park, Md. 20740

[21] Appl. No.: 34,190

[22] Filed: Apr. 27, 1979

[51] Int. Cl.$^3$ ............................................. B01D 15/08
[52] U.S. Cl. .................................. 210/658; 210/198.2
[58] Field of Search ........................... 210/31 C, 198 C

[56] References Cited

U.S. PATENT DOCUMENTS

| | | | |
|---|---|---|---|
| 3,501,009 | 3/1970 | Jaworek | 210/198 C |
| 3,839,205 | 10/1974 | Okumura | 210/198 C |
| 3,856,681 | 12/1974 | Huber | 210/198 C |
| 3,864,250 | 2/1975 | Perry | 210/198 C |
| 3,919,082 | 11/1975 | Falk | 210/198 C |
| 4,139,458 | 2/1979 | Harrison | 210/198 C |

Primary Examiner—John Adee

[57] ABSTRACT

This is an invention of paper chromatography and thin layer chromatography "baw-rar" (where "baw-rar" is Hebrew for separate) cones, hereon called PC and TLC cones, and other geometric shapes whose horizontal cross sections generally decrease in area as they are taken further from the base, with the adsorbent or absorbent layer decreasing in thickness from the base to the apex, to be used in PC and TLC work to reduce the horizontal and vertical spreading and diffusing of the developed spots. These will, for example, provide more easily and definitively determinable $R_f$ values, eliminate scraping of relatively large areas when scraping is necessary and increase the sensitivity of PC and TLC. The methods of use of the new PC and TLC cones are also disclosed herein.

16 Claims, 7 Drawing Figures

THIN LAYER AND PAPER CHROMATOGRAPHY CONES

BRIEF SUMMARY OF THE INVENTION

One of the greatest problems facing the user of PC paper and TLC plates is spreading and diffusing of the developed spot.[1,2] An object and achievment of this invention is to eliminate a large amount of the diffusing of the developed spot by using the new PC and TLC cones or other geometric shapes whose horizontal cross sections as taken further from the base generally decrease in are (FIGS. 1, 2 and 3) and where the PC paper thickness and the TLC adsorbent thickness decrease from the base to the top or apex (FIG. 4).

Reduced horizontal spreading and diffusing of the developed spot is achieved by using such curved PC sheets and TLC plates; the nature of which result in a lateral compression to be experienced by the developing solvent, resulting in reduced horizontal spreading and diffusing of the developed spot.

Reduced vertical spreading and diffusing of the developed spot is achieved by overcoming the resistance to mass transfer by having the paper thickness in the case of PC and the adsorbent thickness in the case of TLC decrease in thickness from the base of the curved sheet or plate where spotting will occur to the top or apex. The initial thicker area reduces the distance the solvent moves per unit time thereby allowing more time for the system to reach equilibrium.

The PC and TLC cones can be made to reduce only horizontal spreading and diffusing or reduce both horizontal and vertical spreading and diffusing of the developed spot. PC cones of uniform paper thickness are known from the literature.[3]

Other objects and benefits achieved by using these new PC and TLC geometrically curved objects are:
  (a) An increased sensitivity in PC and TLC—Because the developed spot will be smaller and therefore more intense and visible, less solute will be needed for visualization.
  (b) Scraping of smaller areas of chromatographic adsorbent when scraping is needed—This is an important advantage when working with toxic chemicals and adsorbent dust production must be minimal.
  (c) Sharper peaks and less background when scanning the developed chromatograms with radioactivity and other scanners.
  (d) Small developed spots will still be obtained when small initial spots cannot be made.
  (e) Specially designed developing tanks and apparatus are not needed—(Although decreased horizontal spreading and diffusing of the developed spots can be achieved by using flat, circular TLC plates, spotting near the outside edge of the plate and developing towards the center, special developing apparatus is needed).[4]

References and examples of prior art include:
1. Shellard, E. J.: *Quantitative Paper and Thin Layer Chromatography*, Academic Press, New York and London, 1968, chapter 1, pages 6–7.
2. Zweig, G. and J. R. Whitaker: *Paper Chromatography and Electrophoresis*, volume 2, Academic Press, New York and London, 1971, pages 12–14, 21–22.
3. ibid., page 65
4. Kaiser, R. E.: "Anticircular High Performance Thin-Layer Chromatography." J. High Resolution Chromatography and Chromatographic Communications 3, 164 (1978).

BRIEF DESCRIPTION OF THE DRAWINGS

The drawings below relate to a preferred embodiment of the invention.

DETAILED DESCRIPTION

Herein, of the different geometric shapes fitting this patent, only the formation and use of the paper and thin layer chromatography cones, hereon called the PC cone and the TLC cone, will be described.

Figure 1:
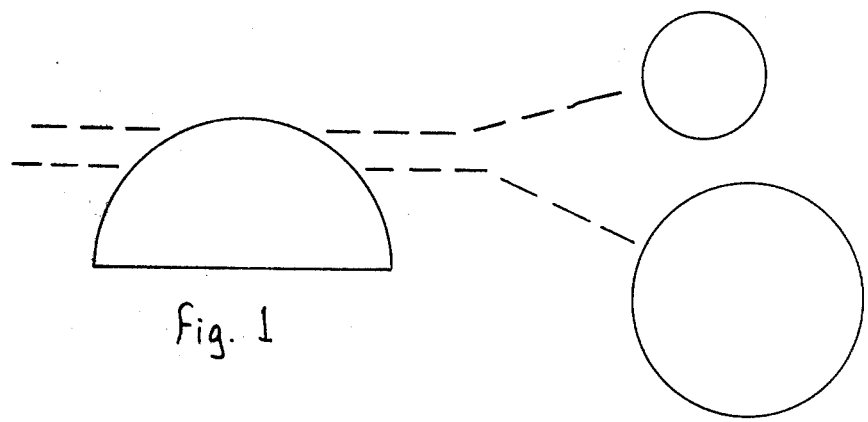
FIGS. 1, 2 and 3 show examples of geometric objects and how their horizontal cross sections generally decrease in area from base to apex.
Figure 2:
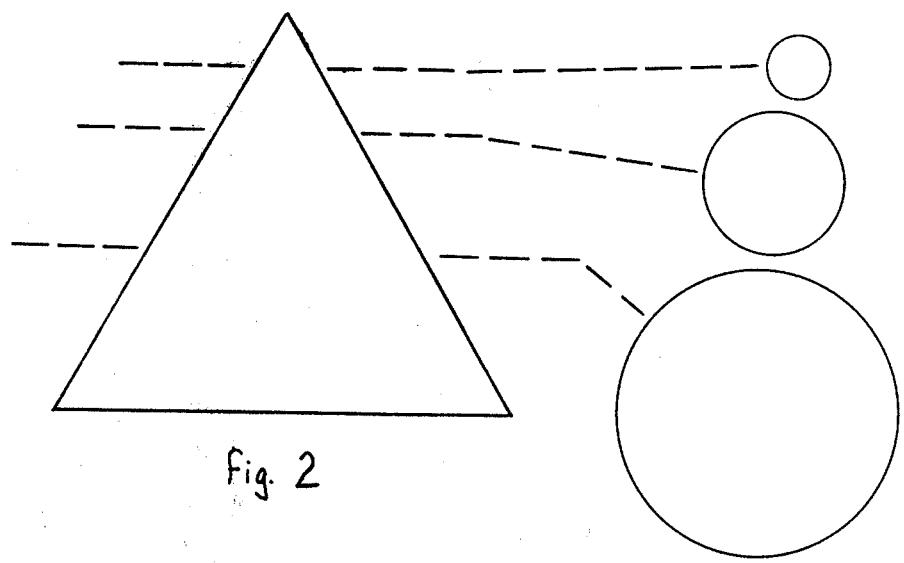
Figure 3:
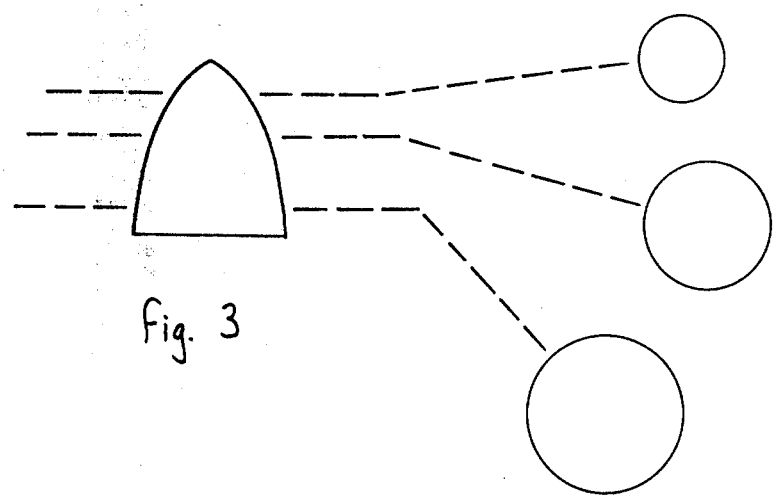
Figure 4:
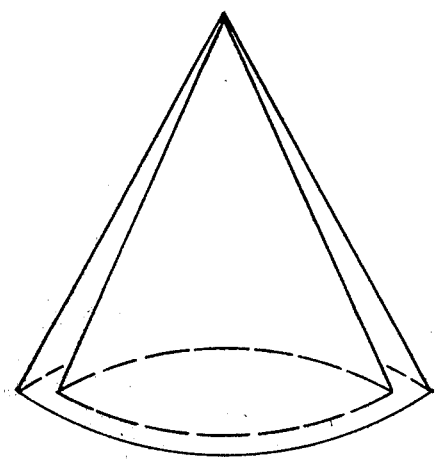
FIG. 4 shows the adsorbent thickness decreasing from base to apex.
Figure 5:
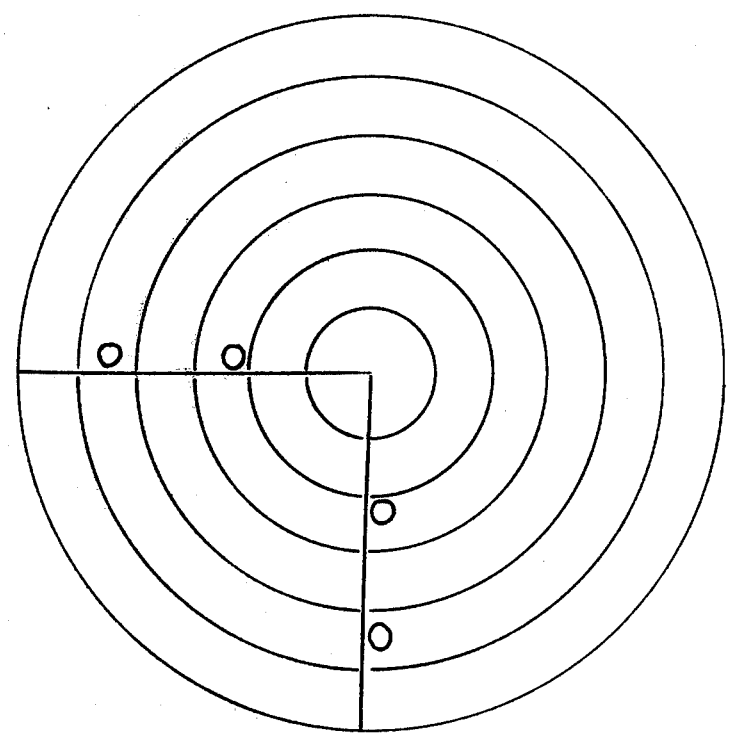
FIG. 5 is an overhead view of a circular TLC plate with a radial section removed and with the needed holes to be clipped so as to form a cone, laying on top of a template with concentric guide cycles.

A preferred embodiment of the TLC cone is made by taking a standard sheet of flexible, plastic, TLC backing (for example 40 cm.×40 cm.) used to make TLC plates, drawing or etching the largest possible circle on it and cutting it out. Pre-cut circular sheets may also be used. About 1 inch from the edge of the flat, plastic circle on the side opposite that which will receive the adsorbent coating is etched or otherwise indelibly drawn a circle which will serve as the guide as to where the initial spots are to placed. Optionally, within this circle can be similarly etched or drawn concentric circles of radii decreasing by 1 centimeter to be used in calculating $R_f$ values, or a template with concentric circles may be used which will eliminate the need for etching or drawing the concentric circles. A ⅛ inch hole is now punched in the center of the flexible backing, a radial section removed similar to taking a piece of pie, 2 holes of 1/16 inch diameter and ⅛ inch from each of the 2 edges resulting from removal of said radial section (FIG. 5) are made and the resulting flexible backing is now fastened to the adsorbent spreader.

The adsorbent spreader is removed and, after drying, spotting is done using the etched or drawn circle on the back of the flexible, plastic backing or a template as a guide. (Spotting may also be done after formation of the cone. This cone formation is described below).

A cone is now formed by bringing the edges containing the holes together and securing the edges as close together as possible without overlapping, placing clips made of material insoluble in TLC solvents (such as the flexible plastic used as a backing in TLC plates) and cuttable with scissors through the holes. The spotted TLC cone is now lowered into the solvent in the developing tank being as careful as possible that all parts of the base touch the solvent simultaneously. After development, the top of the tank is removed and the TLC cone removed. While the TLC cone is drying or after it is dry, the clips are carefully snipped with scissors without disturbing the adsorbrnt while securely holding the seam at the base of the cone between the thumb and forefinger. The cone is now gently collapsed (i.e. opened), any necessary visualizing agent used and then $R_f$ values determined using concentric circles on the back of the collapsed cone or by placing the collapsed cone on a template.

Figure 6:
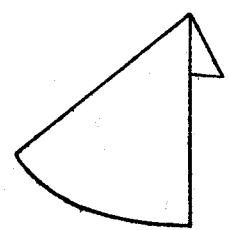
FIGS. 6 and 7 portions of TLC cones made by cutting a TLC cone vertically.
Figure 7:

Alternate methods, such as using portions of TLC cones formed by cutting the cones vertically, are also feasible (FIGS. 6 and 7).

Another method involves using seamless, preformed TLC cones made of standard, flexible, plastic, TLC backing, glass or aluminum. The entire cone is dipped base first in a slurry of the adsorbent, allowed to dry and dipped again but to a shorter depth and repeated as often as desired thereby providing an adsorbent layer of a stepwise decreasing thickness from base to apex.

A conical template placed inside the cone can be used for spotting and $R_f$ determination.

Paper chromatography cones can be made from circular sheets of PC paper where the thickness of the paper decreases going from the outer edge to the center by removing a section of the paper similar to taking a piece of pie (see the parallel description on TLC cones, above), punching holes along the edges formed by removing said section and using clips to keep the paper in conical form.

I claim:

1. A chromatography separation apparatus comprising a member having an apex, with the area of the horizontal cross-section generally decreasing toward the apex, said member being constructed of a material including silica gel and said member selected from the group consisting of at least part of a cone, hemisphere or paraboloid.

2. the chromatography separation apparatus of claim 1 wherein the thickness of the material generally decreases toward the apex.

3. The chromatography separation apparatus of claim 1 wherein the thickness of the material is uniform.

4. The chromatography separation apparatus of claim 1 where the material going in the direction from base to apex is composed of bands of materials of different properties which affect the rate of solvent flow.

5. The chromatography separation apparatus of claim 1 wherein the said member is a shell.

6. A chromatography separation apparatus comprising a member having an apex with the area of the horizontal cross-section generally decreasing toward the apex, said member being constructed of a material including an adsorbent or absorbent and said member selected from the group consisting of at least part of a cone, hemisphere or paraboloid, wherein the thickness of the material generally decreases toward the apex.

7. The chromatography separation apparatus of claim 6 where the material comprises paper.

8. The chromatography separation apparatus of claim 6 where the said material, going in the direction from base to apex, is composed of bands of materials of different properties which affect the rate of solvent flow.

9. A chromatographic method of separating components of a material comprising: (1) application of a liquid containing said componets to a member having an apex, with a generally decreasing horizontal cross-section toward the apex, wherein said member comprises paper, and (2) developing the member by inserting it in a solvent such that the componets separate.

10. The chromatographic method of claim 9 wherein said member is a shell.

11. The chromatographic method of claim 9 whereby the member containing the components at some degree of separation is cut or scraped to remove the part of the member containing the componet.

12. A chromatographic method of separating componets of a material comprising: (1) application of a liquid containing said componets to a member having an apex, with a generally decreasing horizontal cross-section toward the apex, wherein said member is coated with an adsorbent, and (2) developing the member by inserting it in a solvent such that the componets separate.

13. The chromatographic method of claim 12, wherein the said member is coated with an adsorbent at a uniform thickness.

14. The chromatographic method of claim 12, wherein said member is a shell.

15. The chromatographic method of claim 12, whereby the member containing the componets at some degree of separation is cut or scraped to remove the part of the member containing the componet.

16. The chromatographic method of claim 12, wherein the said member is coated with an adsorbent of a thickness generally decreasing toward the apex.

* * * * *